US008021623B2

(12) United States Patent
Oikawa et al.

(10) Patent No.: US 8,021,623 B2
(45) Date of Patent: Sep. 20, 2011

(54) EXAMINATION METHOD AND EXAMINATION ASSISTANT DEVICE FOR QUARTZ PRODUCT OF SEMICONDUCTOR PROCESSING APPARATUS

(75) Inventors: Masayuki Oikawa, Mizusawa (JP); Katsuhiko Anbai, Esashi (JP); Nobuhiro Takahashi, Kai (JP); Teruyuki Hayashi, Kofu (JP)

(73) Assignee: Tokyo Electron Limited, Tokyo (JP)

( * ) Notice: Subject to any disclaimer, the term of this patent is extended or adjusted under 35 U.S.C. 154(b) by 1255 days.

(21) Appl. No.: 10/574,286

(22) PCT Filed: Sep. 6, 2004

(86) PCT No.: PCT/JP2004/012953
§ 371 (c)(1),
(2), (4) Date: Mar. 31, 2006

(87) PCT Pub. No.: WO2005/036135
PCT Pub. Date: Apr. 21, 2005

(65) Prior Publication Data
US 2007/0008638 A1    Jan. 11, 2007

(30) Foreign Application Priority Data
Oct. 8, 2003    (JP) .................................. 2003-349892

(51) Int. Cl.
*G01N 1/32* (2006.01)
*H01L 21/00* (2006.01)
(52) U.S. Cl. ........ 422/300; 422/292; 422/301; 422/500; 134/117; 134/104.1; 118/421; 118/404
(58) Field of Classification Search .................... 422/50, 422/68.1, 82.05, 99, 104, 102, 255, 261, 422/266, 292, 500, 547, 566, 300, 301; 436/73; 134/117, 150, 73, 75, 82, 83, 85, 92, 104.1, 134/165; 216/83, 84, 100, 8, 10; 118/400, 118/404, 427, 421
See application file for complete search history.

(56) References Cited

U.S. PATENT DOCUMENTS
2003/0000458 A1 * 1/2003 Marumo et al. .............. 117/200

FOREIGN PATENT DOCUMENTS
| JP | 9-257669 | 10/1997 |
| JP | 2001-66232 | 3/2001 |
| JP | 2001-77158 | 3/2001 |
| JP | 2001-223251 | 8/2001 |
| JP | 2001-242052 | 9/2001 |
| JP | 2003-202278 | 7/2003 |
| JP | 2003-522708 | 7/2003 |
| KR | 2000-0020879 | 4/2000 |

* cited by examiner

*Primary Examiner* — Jill Warden
*Assistant Examiner* — Cedric Chan
(74) *Attorney, Agent, or Firm* — Oblon, Spivak, McClelland, Maier & Neustadt, L.L.P.

(57) ABSTRACT

An examination assistant device (3) is used for examination in which a process solution containing an etching solution is held in contact with an examination objective portion of a quartz pole member (21) of a semiconductor processing apparatus, and then the process solution is analyzed to identify a metal impurity contained in the examination objective portion. The pole member (21) includes a pair of concave portions (22) disposed one on either side of the examination objective portion. The examination assistant device (3) includes a pair of end plates (32) configured to engage with the pair of concave portions, a frame (30) connecting the pair of end plates, and a solution receiver (31) disposed between the pair of end plates. The solution receiver (31) has dimensions to store the process solution and hold the process solution in contact with the examination objective portion.

18 Claims, 12 Drawing Sheets

| HF concentration (wt%) | 5 | 10 | 25 |
|---|---|---|---|
| Etching time (min) | 35 | 15 | 5 |

| | | Na | Al | Cr | Fe | Ni | Cu | Zn |
|---|---|---|---|---|---|---|---|---|
| AAS | Measurement value (ng) | 0.05 | 0.24 | 0.08 | 0.17 | 0.14 | 0.08 | 0.02 |
| | Converted value (ppb) | 22.5 | 108 | 36 | 76.5 | 63 | 36 | 9 |
| ICP-MS | Measurement value (ng) | 0.006 | 0.027 | 0.015 | 0.016 | 0.006 | 0.01 | 0.012 |
| | Converted value (ppb) | 2.7 | 12.2 | 6.8 | 7.2 | 2.7 | 4.5 | 5.4 |

F I G. 11

F I G. 12

EXAMINATION METHOD AND EXAMINATION ASSISTANT DEVICE FOR QUARTZ PRODUCT OF SEMICONDUCTOR PROCESSING APPARATUS

TECHNICAL FIELD

The present invention relates to an examination method for identifying a metal impurity contained in an examination objective portion of a quartz product used in a semiconductor processing apparatus, and an examination assistant device used in the method. Examples of the quartz product are a reaction tube, a substrate holder, and a thermal insulation member, which are exposed to the process atmosphere of a heat processing apparatus. The term "semiconductor process" used herein includes various kinds of processes which are performed to manufacture a semiconductor device or a structure having wiring layers, electrodes, and the like to be connected to a semiconductor device, on a target substrate, such as a semiconductor wafer or a glass substrate used for an LCD (Liquid Crystal Display) or FPD (Flat Panel Display), by forming semiconductor layers, insulating layers, and conductive layers in predetermined patterns on the target substrate.

BACKGROUND ART

In manufacturing semiconductor devices, various processing apparatuses are used to subject a target substrate, such as a semiconductor wafer, to processes, such as CVD (Chemical Vapor Deposition), oxidation, diffusion, reformation, annealing, and etching. As processing apparatuses of this kind, vertical heat processing apparatuses are known to subject a number of wafers together to a heat process. In general, vertical heat processing apparatuses have a vertical airtight reaction tube (process chamber) for accommodating wafers. The reaction tube has a load port formed at the bottom, which is selectively opened and closed by a lid moved up and down by an elevator. Within the reaction tube, the wafers are supported at intervals in the vertical direction on a holder called a wafer boat. The wafer boat is loaded and unloaded to and from the reaction tube through the load port by the elevator while the wafer boat holds the wafers and is supported on the lid.

In vertical heat processing apparatuses, metal contamination may occur such that a metal impurity is mixed into a thin film on the wafer surface, although it is in a very small amount. With the increase in the degree of density and integration of semiconductor devices, the thickness of films in the semiconductor devices is becoming smaller, and the device characteristics become more sensitive to metal contamination. Accordingly, it is necessary to take countermeasures against such metal contamination in order to improve the device characteristics. In this respect, the present inventors have found that this metal contamination is associated with metal impurities contained in quartz products, such as reaction tubes, wafer boats, and thermal insulation cylinders for supporting wafer boats.

DISCLOSURE OF INVENTION

An object of the present invention is to identify, by means of nondestructive examination, a metal impurity contained in an examination objective portion of a quartz product used in a semiconductor processing apparatus.

According to a first aspect of the present invention, there is provided an examination assistant device used for examination in which a process solution comprising an etching solution is held in contact with an examination objective portion of a quartz pole member of a semiconductor processing apparatus, and then the process solution is analyzed to identify a metal impurity contained in the examination objective portion, wherein the pole member includes a pair of concave portions disposed one on either side of the examination objective portion, the device comprising:

a pair of end plates configured to engage with the pair of concave portions;

a frame connecting the pair of end plates; and a solution receiver disposed between the pair of end plates, and having dimensions to store the process solution and hold the process solution in contact with the examination objective portion.

According to a second aspect of the present invention, there is provided an examination assistant device used for examination in which a process solution comprising an etching solution is held in contact with an examination objective portion of a quartz reaction tube of a semiconductor processing apparatus, and then the process solution is analyzed to identify a metal impurity contained in the examination objective portion, wherein the quartz reaction tube includes a curved surface on which the examination objective portion is positioned, the device comprising:

an annular member having a bottom surface to come into close contact the curved surface, and configured to cooperate with the curved surface to form a solution receiver that surrounds the examination objective portion for storing the process solution.

According to a third aspect of the present invention, there is provided an examination method for identifying a metal impurity contained in an examination objective portion of a quartz product of a semiconductor processing apparatus, the method comprising:

placing on the quartz product an examination assistant device configured to form a solution receiver to hold a liquid in contact with the examination objective portion;

causing a process solution comprising an etching solution within the solution receiver to be in contact with the examination objective portion for a predetermined time, thereby performing etching on the examination objective portion; and operating an analyzer to analyze the process solution used for the etching, thereby identifying the metal impurity contained in the examination objective portion.

BEST MODE FOR CARRYING OUT THE INVENTION

In the process of developing the present invention, the inventors studied metal contamination of wafers caused in vertical heat processing apparatuses. As a result, the inventor has arrived at the findings given below.

Quartz products, such as a reaction tube, a wafer boat, and a thermal insulation cylinder, contain metal impurities, such as copper and iron, although they are in a small amount. The metal impurities may originate from those contained in quartz material from the beginning, or those mixed during the process of machining the quartz material. If a heat process is performed on wafers W, using a quartz product containing a metal impurity, the metal impurity is desorbed from the quartz product and diffused within the process atmosphere. Consequently, metal contamination occurs such that the metal impurity is mixed into a thin film on a wafer surface, although it is in a very small amount.

With the increase in the degree of density and integration of semiconductor devices, the thickness of films in the semiconductor devices is increasingly becoming, and thus the device characteristics have become more sensitive to metal contamination. Accordingly, it is necessary to examine the metal impurity concentration in the surface layer of a quartz product in advance, so as to guarantee the specification of the apparatus in question. Further, in order to safely use a new quartz product or cleaned quartz product, it is necessary to achieve an analysis technique with high accuracy, which ensures that the quartz product in use will not cause contamination of wafers W.

For example, Patent Document 1 (PCT National Publication No. 2003-522708 (see the first embodiment and FIGS. 1 and 2)) and Patent Document 2 (Jpn. Pat. Appln. KOKAI Publication No. 2001-223251 (see the first embodiment and FIGS. 1 and 2)) disclose methods for determining a metal impurity concentration in a quartz sample piece. According to these methods, the sample piece is immersed in an etching solution, such as hydrofluoric acid, to dissolve the metal impurity into the etching solution. Then, the etching solution is analyzed by an analyzer, such as an atomic absorption analyzer (AAS), inductively coupled plasma atomic emission analyzer (ICP-AES), or inductively coupled plasma mass analyzer (ICP-MS). By doing so, the metal impurity concentration in the sample piece is determined.

Where the methods disclosed in Patent Document 1 and Patent Document 2 are applied to a semiconductor processing apparatus, such as a vertical heat processing apparatus, a sample piece needs to be cut out from a quartz product. This is so because the quartz products of a vertical heat processing apparatus, such as a reaction tube and a wafer boat, are large in general. Accordingly, if the quartz products are intact, it is difficult to etch an examination objective portion thereof and collect the etching solution. For this reason, the methods described above require a sample piece to be prepared in advance of the examination, by such an operation that a reaction tube is put in a polyethylene bag and crushed by a hammer, or a part of a wafer boat is cut out.

At present, since a quartz product that has caused metal contamination of wafers W cannot be reused, there is no waste incurred even if such a quartz product is crushed. However, recently, a cleaning technique using, e.g., hydrogen chloride gas is being established for cleaning quartz products. Thus, it is necessary to use nondestructive examination for identifying a metal impurity contained in an examination objective portion of quartz products, which allows the quartz products to be reused. Further, where a sample piece is immersed in an etching solution, a metal impurity in a cut surface of the sample piece is dissolved into the etching solution. In this case, it is difficult to detect the metal impurity in the examination objective portion with high accuracy.

Embodiments of the present invention achieved on the basis of the findings given above will now be described with reference to the accompanying drawings. In the following description, the constituent elements having substantially the same function and arrangement are denoted by the same reference numerals, and a repetitive description will be made only when necessary.

Figure 12:
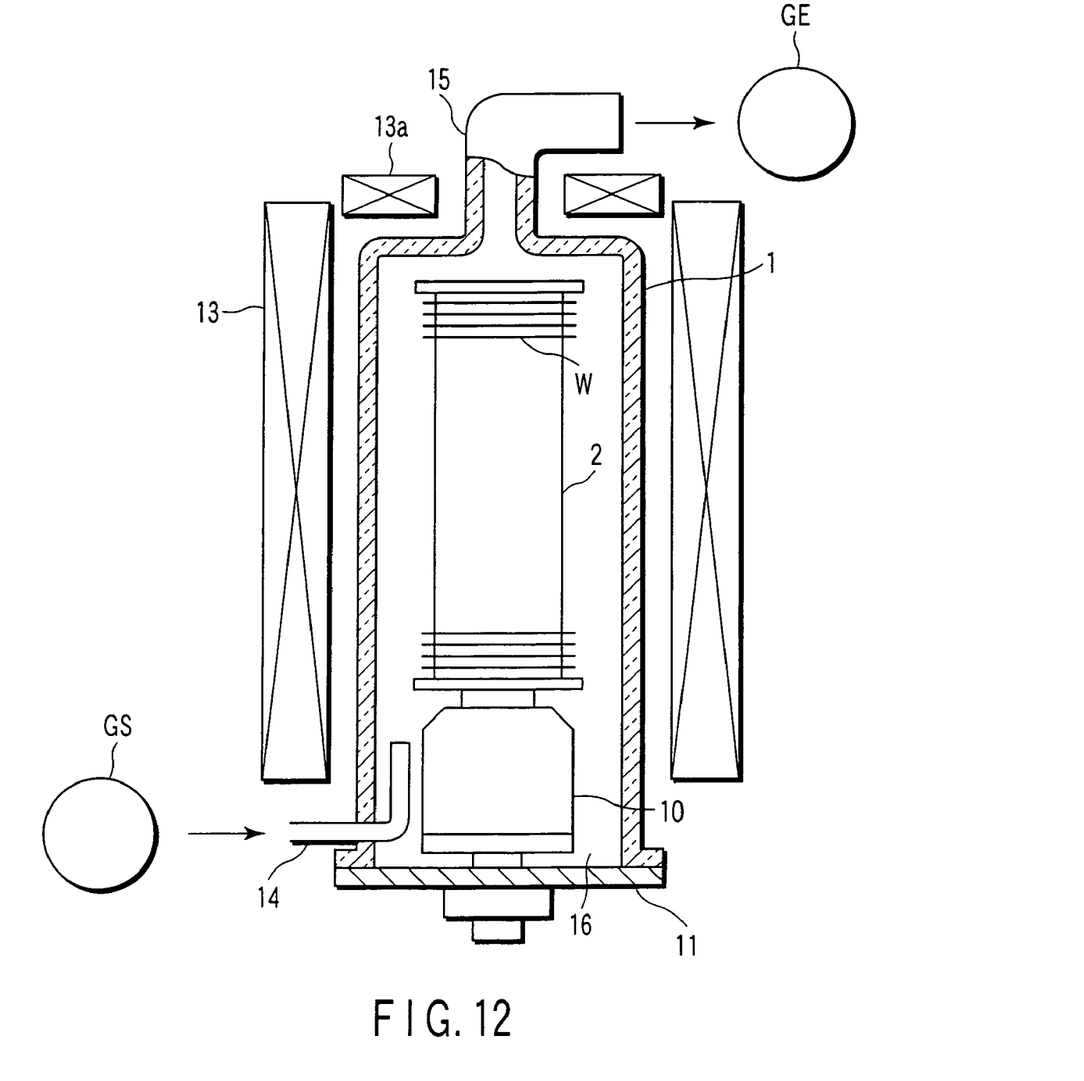
FIG. 12 is a view schematically showing a vertical heat processing apparatus for performing a heat process (an oxidation process in this example) on semiconductor wafers.

FIG. 12 is a view schematically showing a vertical heat processing apparatus for performing a heat process (an oxidation process in this example) on semiconductor wafers. As shown in FIG. 12, this processing apparatus includes a vertical reaction tube (process chamber) 1 made of quartz to form a heat process atmosphere for target substrates or semiconductor wafers W. The reaction tube 1 has a load port 16 formed at the bottom, which is opened and closed by a lid 11 movable up and down. A wafer boat (substrate holder) 2 for supporting wafers W is detachably supported on the lid 11 through a thermal insulator or thermal insulation cylinder 10. The thermal insulation cylinder 10 and wafer boat 2 are made of quartz. For example, the wafer boat 2 can support 25 to 50 wafers at intervals in the vertical direction.

Heaters 13 and 13a are disposed around the reaction tube 1 to heat the atmosphere within the reaction tube 1 (to, e.g., 1,000° C. for an oxidation process). A process gas supply line 14 is inserted into the reaction tube 1 through the sidewall near the bottom, for supplying process gases (including, e.g., hydrogen gas and oxygen gas) into the reaction tube 1. The process gas supply line 14 is connected to a process gas supply source GS through a mass flow controller (MFC) (not shown). On the other hand, an exhaust port 15 is formed at the top of the reaction tube 1 and connected to an exhaust section GE including a vacuum exhaust pump and so forth. The exhaust section GE is used to exhaust the atmosphere within the reaction tube 1, and set it at a predetermined pressure (vacuum level).

Figure 1:
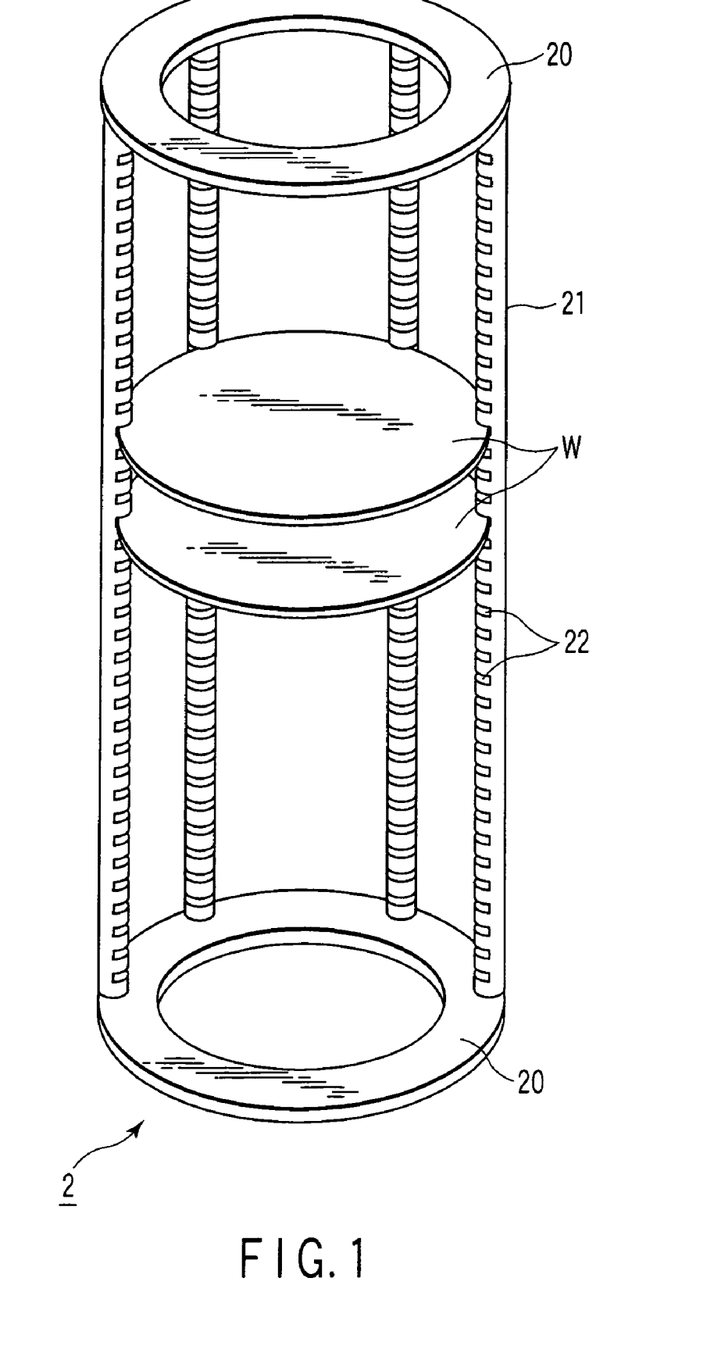
FIG. 1 is a perspective view showing a wafer boat (substrate holder) used in an apparatus shown in FIG. 12.

FIG. 1 is a perspective view showing the wafer boat (substrate holder) 2 used in the apparatus shown in FIG. 12. As shown in FIG. 1, for example, the wafer boat 2 includes annular support plates 20 disposed at the top and bottom, and a plurality of, e.g., four, supporting struts (pole members) 21 connecting the support plates 20. The support plates 20 and supporting struts 21 are made of quartz. Each of the supporting struts 21 has a number of grooves (concave portions) 22 arrayed at intervals in the vertical direction, such that the height levels of the grooves are the same among the four supporting struts 21. Each of the wafers W is horizontally supported while the edge thereof is inserted into grooves 22 of the four supporting strut 21 at the same level.

Figure 2:
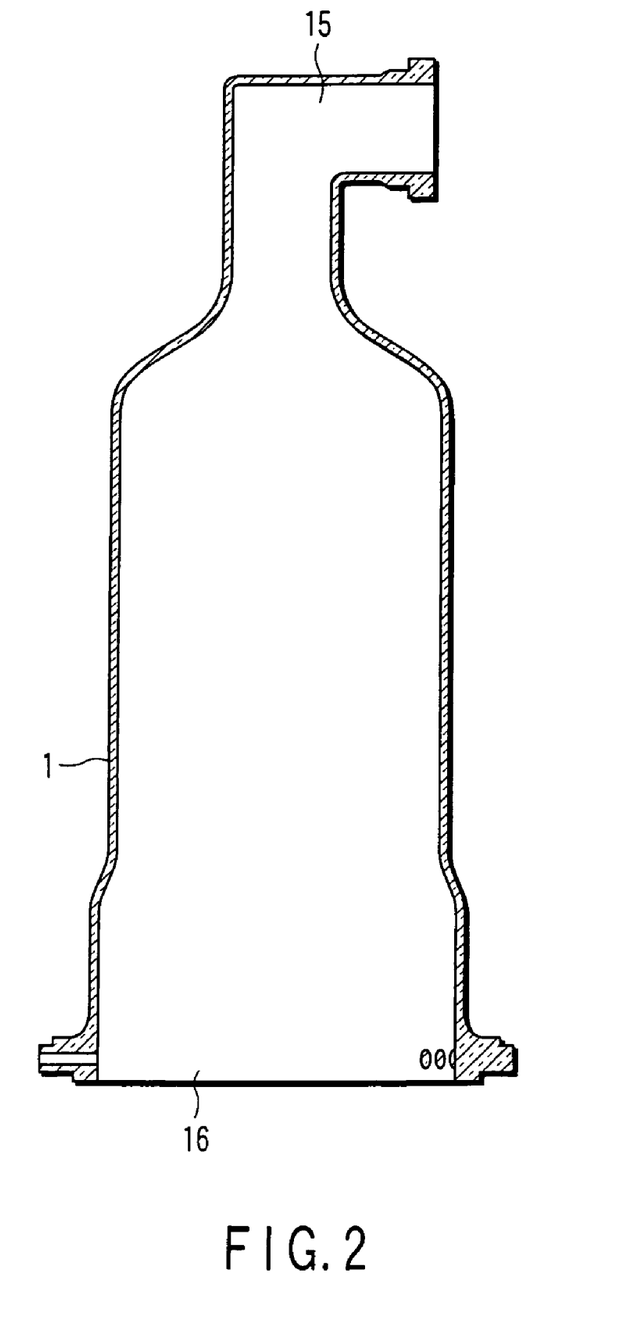
FIG. 2 is a sectional side view showing a reaction tube (process chamber) used in an apparatus shown in FIG. 12.

FIG. 2 is a sectional side view showing the reaction tube (process chamber) 1 used in the apparatus shown in FIG. 12. As shown in FIG. 2, the reaction tube 1 is formed of a quartz cylindrical body that has an exhaust port 15 at the top and a load port 16 at the bottom. The wafer boat 2 shown in FIG. 1 is loaded and unloaded to and from the reaction tube 1 through the load port 16.

Figure 3A:
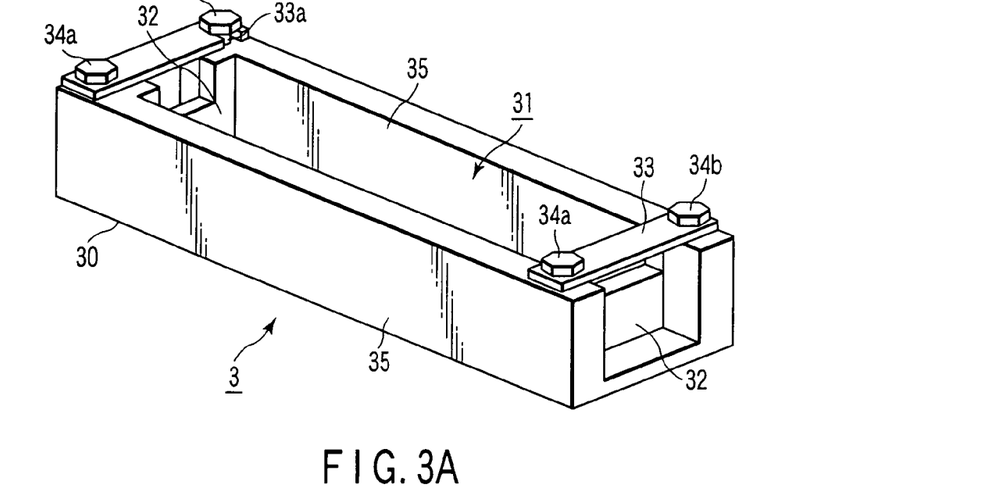
FIG. 3A is a perspective view showing an examination assistant device used for examination to identify a metal impurity contained in the surface layer of a supporting strut of the wafer boat.
Figure 3B:
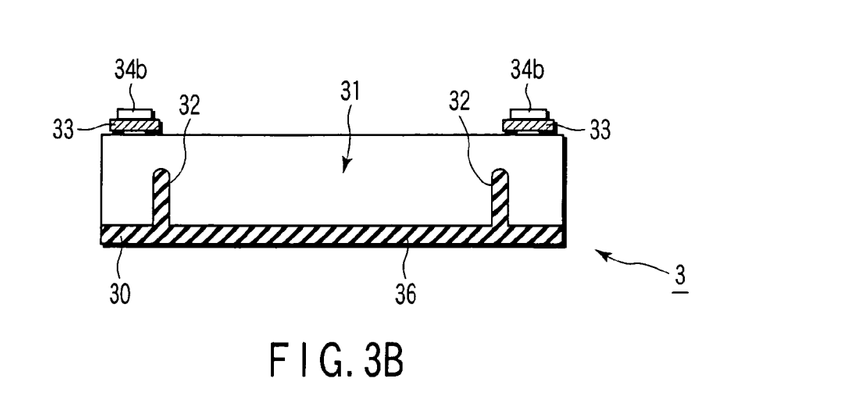
FIG. 3B is a sectional side view of the examination assistant device shown in FIG. 3A.
Figure 3C:
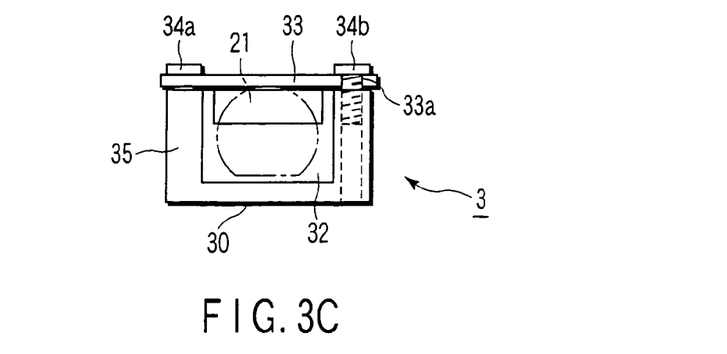
FIG. 3C is an end side view of the examination assistant device shown in FIG. 3A.

FIGS. 3A to 3C are a perspective view, a sectional side view, and an end side view showing an examination assistant device 3 used for examination to identify a metal impurity contained in the surface layer of a supporting strut 21 of the wafer boat 2. As shown in FIGS. 3A to 3C, the examination assistant device 3 includes a frame 30 formed as a rectangular vessel. The frame 30 is preferably made of a corrosion resistant material, such as a fluoroplastic, e.g., PFA or PTFE, against an etching solution described later.

The frame 30 includes a pair of end plates 32 disposed on the near inside of the opposite ends. The pair of end plates 32 cooperate with a pair of side plates 35 and a bottom plate 36 to form a liquid-tight solution receiver 31. The solution receiver 31 is configured and sized to store a process solution consisting of an etching solution described later, and to hold the process solution in contact with an examination objective portion of the supporting strut 21. The pair of end plates 32 are arranged to be inserted into two grooves (concave portion) 22 of the supporting strut 21 separated from each other at a predetermined distance. The side plates 35 have height larger than that of the end plates 32 and larger than the dimension from the front to the back of the supporting strut 21 (see FIG. 3). When the end plates 32 are inserted into the two grooves 22 of the supporting strut 21, a portion between the two grooves 22 treated as an examination objective portion is immersed in the process solution stored in the solution receiver 31.

The opposite ends of the side plates 35 extend outward from the end plates 32. A latch 33 is disposed to bridge the two side plates 35 at each of the opposite ends of the side plates 35, for attaching the examination assistant device 3 to the supporting strut 21. When the examination assistant device 3 is attached to the supporting strut 21, the supporting strut 21 is pinched between the pair of latches 33 and the pair of end plates 32. The proximal end of each latch 33 is pivotally supported on the upper surface of one of the side plates 35 by a screw 34a. On the other hand, the distal end of each latch 33 has a notch 33a formed to engage with the screw 34b disposed on the upper surface of the other of the side plates 35. Accordingly, each latch 33 can rotate about the screw 34a as a center between a position to attach the examination assistant device 3 to the supporting strut 21 (where the notch 33a engages with the screw 34b), and a position to detach the examination assistant device 3 from the supporting strut 21 (where the notch 33a disengages from the screw 34b).

Figure 4A:
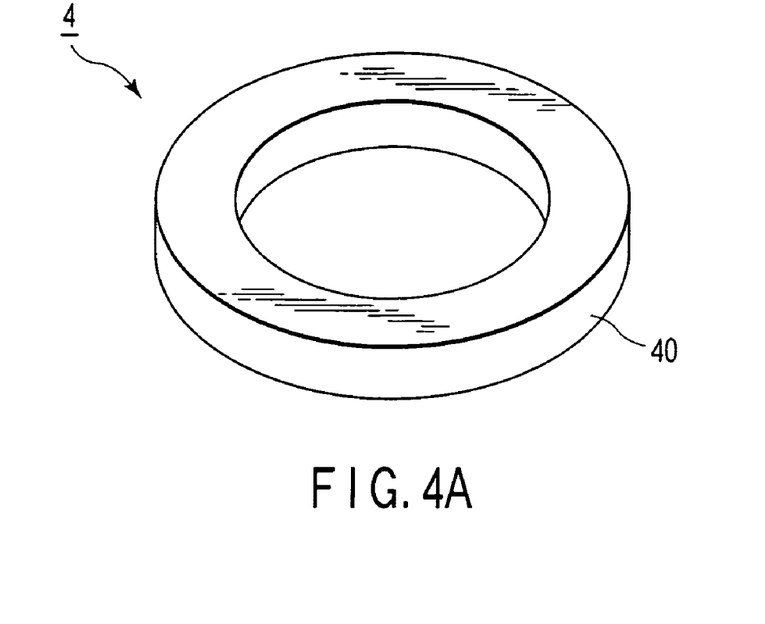
FIG. 4A is a perspective view showing an examination assistant device used for examination to identify a metal impurity contained in the surface layer of an curved inner surface of the reaction tube.
Figure 4B:
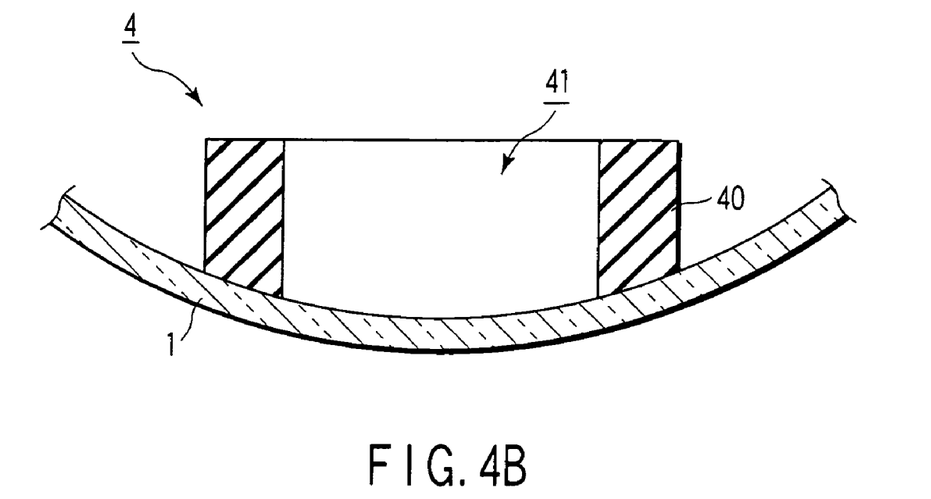
FIG. 4B is a sectional side view of the examination assistant device shown in FIG. 4A.

FIGS. 4A and 4B are a perspective view and a sectional side view, respectively, showing an examination assistant device 4 used for examination to identify a metal impurity contained in the surface layer of an curved inner surface of the reaction tube 1. As shown in FIG. 4A, the examination assistant device 4 is formed of an annular member 40, which is preferably made of a corrosion resistant material, such as a fluoroplastic, e.g., PFA or PTFE, against an etching solution described later. As shown in FIG. 4B, the annular member 40 is configured to cooperate with a curved inner surface of the reaction tube 1 to form a solution receiver 41, which surrounds an examination objective portion and stores a process solution consisting of an etching solution described later. In order to achieve this, the bottom of the annular member 40 is formed as a convex curved surface (which is a complementary shape to the curved inner surface of the reaction tube 1), so that it comes into liquid-tight contact with the curved inner surface of the reaction tube 1 without a gap therebetween.

For example, where the examination assistant device 4 is directed to the cylindrical side wall of the reaction tube 1 as an examination objective portion, the curvature of the bottom surface of the annular member 40 is set to be small. Where the examination assistant device 4 is directed to the neck portion at the exhaust port 15 of the reaction tube 1 as an examination objective portion, the curvature of the bottom surface of the annular member 40 is set to be large. As described above, the bottom surface of the annular member 40 comes into close contact with an inner surface of the reaction tube 1, and the bottom opening of the annular member 40 is thereby closed to form a solution receiver 41, the a bottom surface of which is the inner surface of the reaction tube 1. The annular member 40 has a thickness and diameter set to store a predetermined amount of the process solution.

Figure 5A:
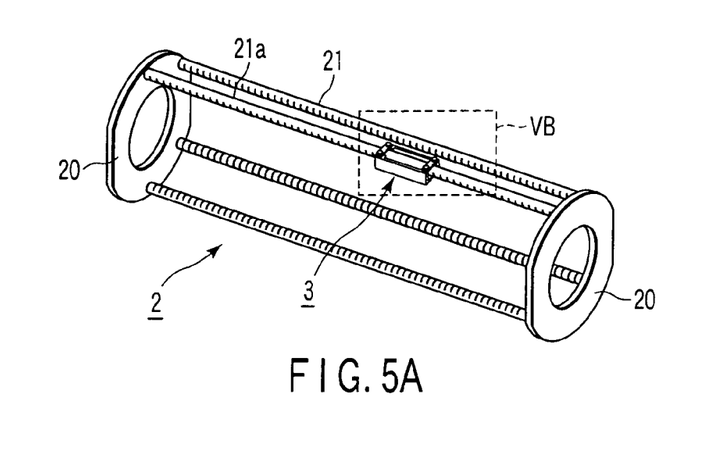
FIG. 5A is a view showing a step of examination to identify a metal impurity contained in the surface layer of a supporting strut of the wafer boat, using the examination assistant device.
Figure 5B:
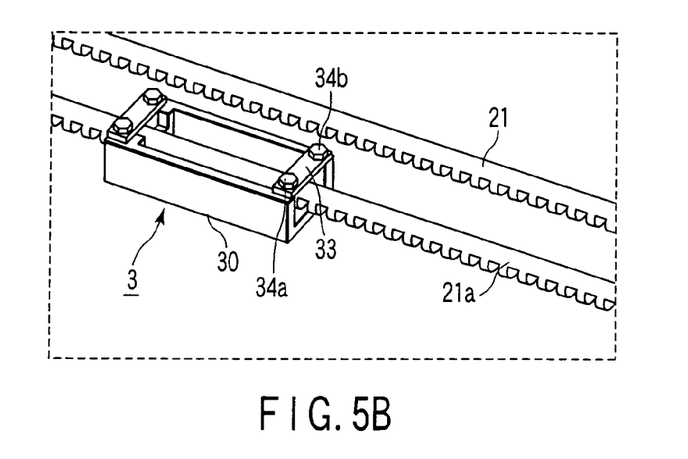
FIG. 5B is an enlarged perspective view showing a portion VB in FIG. 5A.
Figure 5C:
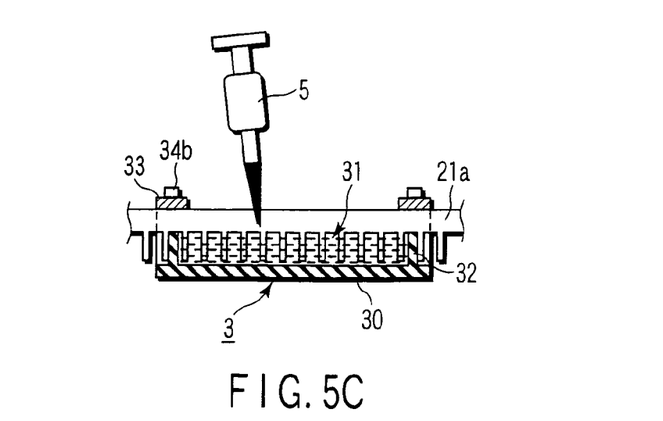
FIG. 5C is a view showing a step of the examination following FIG. 5A.

Next, an explanation will be give of a method of using the examination assistant device 3. FIGS. 5A and 5C are views showing steps of examination to identify a metal impurity contained in the surface layer of the supporting strut 21 of the wafer boat 2, using the examination assistant device 3. FIG. 5B is an enlarged perspective view showing a portion VB in FIG. 5A.

At first, as shown in FIGS. 5A and 5B, the wafer boat 2 is horizontally placed so that the grooves 22 formed in that supporting strut 21a, which includes an examination objective portion, face down. Then, the examination assistant device 3 is transferred, while both the latches 33 are in the open state, to engage with the wafer boat 2 in this state, such that the end plates 32 are inserted into certain grooves 22 of the supporting strut 21a from below. Then, the latches 33 are rotated into the closed state (the notches 33a of the latches 33 engage with the screws 34b), to attach and fix the examination assistant device 3 to the supporting strut 21a. At this time, the examination assistant device 3 is preferably set such that the frame 30 is in a horizontal state as far as possible.

After the examination assistant device 3 is fixed to the supporting strut 21a, as shown in FIG. 5C, the process solution consisting of an etching solution is supplied into the solution receiver 31 of the examination assistant device 3, using an injector 5, such as a dropper or micro-syringe. For example, the process solution (etching solution) contains 0 to 10 wt % of nitric acid and 0.5 to 25 wt % of hydrofluoric acid. The amount L1 of the process solution is set at a value of, e.g., 0.5 to 40 ml, with which the examination objective portion (a portion of the supporting strut 21 including grooves 22) can be immersed in the process solution in the solution receiver 31. The solution receiver 31 may be supplied with a predetermined amount of the process solution before the examination assistant device 3 is attached to the supporting strut 21a.

Figure 6:
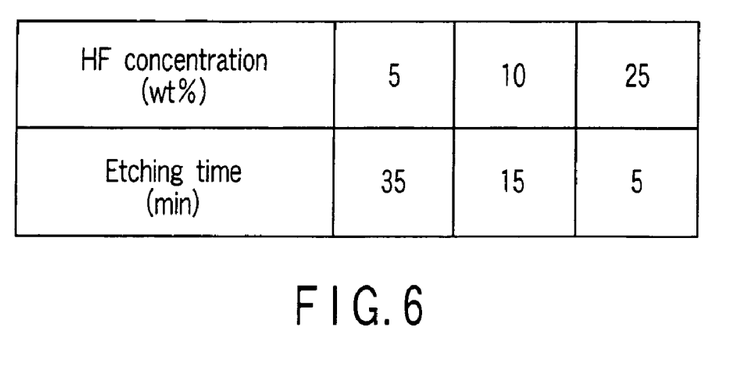
FIG. 6 is a view showing the relationship between the hydrofluoric acid concentration and etching time in etching quartz to a depth of 1 μm from the surface.

FIG. 6 is a view showing the relationship between the hydrofluoric acid concentration and etching time in etching quartz to a depth of 1 μm from the surface. The process described above is performed with reference to such a relationship between the composition of the process solution and the process time to form a predetermined etching depth, which is obtained by an experiment conducted in advance. Accordingly, the examination objective portion is immersed in the process solution and thereby etched for a predetermined time at room temperature and at atmospheric pressure. The quartz and metal impurity of the examination objective portion immersed in the process solution are dissolved into the process solution. If the concentration of hydrofluoric acid is too high, it bubbles intensively and hinders etching from being performed with high planar uniformity. If the concentration of hydrofluoric acid is too low, it takes a long time to complete the etching. In light of these factors, it is preferable to perform the etching for 15 minutes at room temperature and at atmospheric pressure, using a solution containing 0.1 wt % of nitric acid and 10 wt % Of hydrofluoric acid.

Figure 7A:
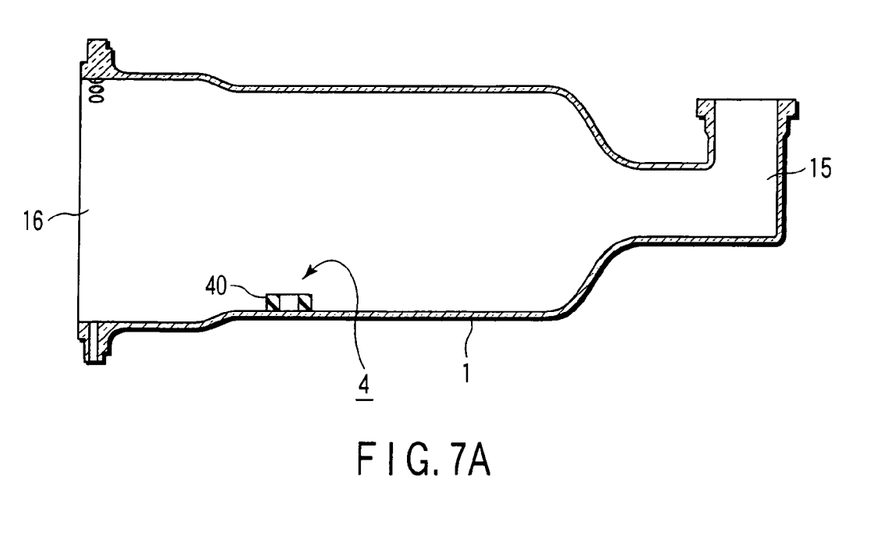
FIG. 7A is a view showing a step of examination to identify a metal impurity contained in the surface layer of a curved inner surface of the reaction tube, using the examination assistant device.
Figure 7B:
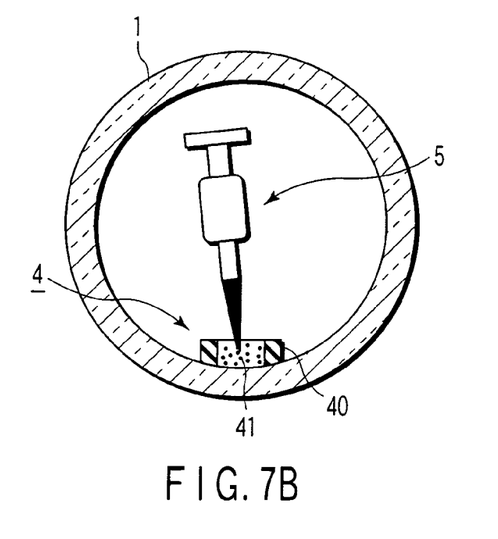
FIG. 7B is a view showing a step of the examination following FIG. 7A.
Figure 8A:
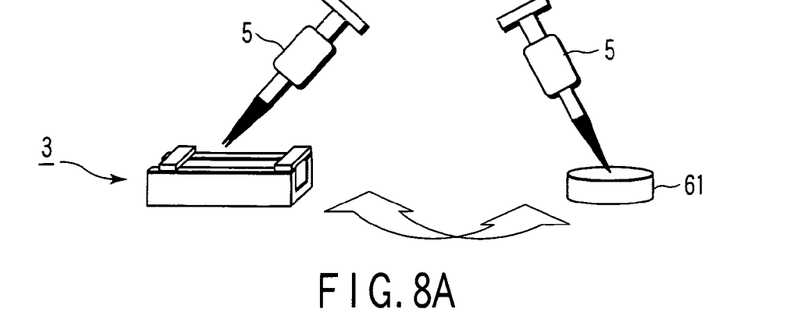
FIG. 8A is a view showing a step of analyzing the process solution after etching.
Figure 8B:
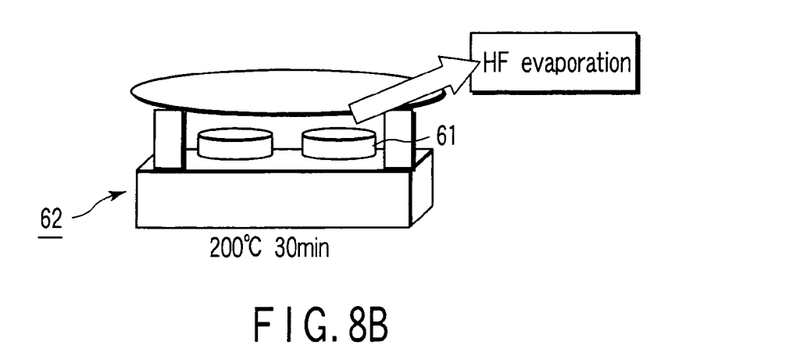
FIG. 8B is a view showing a step of the examination following FIG. 8A.
Figure 8C:
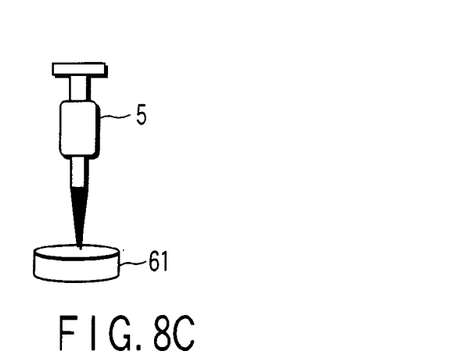
FIG. 8C is a view showing a step of the examination following FIG. 8B.
Figure 8D:
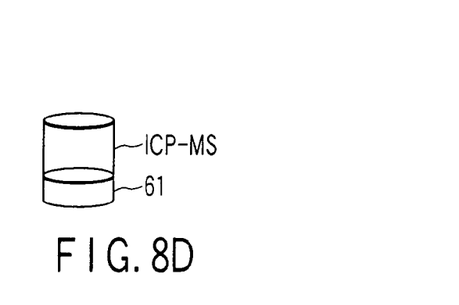
FIG. 8D is a view showing a step of the examination following FIG. 8C.

Next, an explanation will be given of a method of using the examination assistant device 4. FIGS. 7A and 7B are views showing steps of examination to identify a metal impurity contained in the surface layer of a curved inner surface of the reaction tube 1, using the examination assistant device 4.

At first, as shown in FIG. 7A, the reaction tube 1 is horizontally placed so that, for example, the exhaust port 15 is directed vertically upward. Then, the examination assistant device 4 is transferred through the load port 16 into the reaction tube 1 in this state, and the annular member 40 of the examination assistant device 4 is placed on a curved inner surface. At this time, the bottom surface of the annular member 40 comes into close contact with the curved inner surface of the reaction tube 1 to form a solution receiver 41 surrounding the examination objective portion.

After the examination assistant device 4 is placed on the curved inner surface of the reaction tube 1, as shown in FIG. 7B, the process solution consisting of an etching solution is supplied into the solution receiver 41, using an injector 5, such as a dropper or micro-syringe. The composition and supply amount of the process solution and the process time are the same as those in the examination assistant device 3 described with reference to FIGS. 5A to 5C.

Thereafter, the process solution used for the etching is analyzed by an analyzer, such as an atomic absorption analyzer (AAS), inductively coupled plasma atomic emission analyzer (ICP-AES), or inductively coupled plasma mass analyzer (ICP-MS). This analysis step is common to both the examination assistant devices 3 and 4. FIGS. 8A to 8D are views showing steps of analyzing the process solution after etching.

At first, as shown in a step S1 of FIG. 8, a process solution (primary process solution) in the solution receiver 31 (41) is transferred by, e.g., an injector 5 to another container, such as an evaporating pan 61, (collection operation). Then, as shown in a step S2 of FIG. 8, the evaporating pan 61 is placed in a heating atmosphere, which is formed by an evaporator 62 and set at, e.g., 200° C., for, e.g., 30 minutes. Consequently, water, hydrogen fluoride, and nitric acid contained in the process solution are evaporated, so that the quartz and metal impurity are precipitated. Then, the evaporating pan 61 is taken out of the heating atmosphere and naturally cooled to, e.g., room temperature.

Then, as shown in a step S3 of FIG. 8, the precipitated product of the quartz and metal impurity on the evaporating pan 61 are dissolved into a secondary process solution (solvent) consisting of an etching solution. For example, the secondary process solution (etching solution) is diluted hydrofluoric acid containing 1 wt % or less of hydrogen fluoride and nitric acid. The secondary process solution is used in an amount L2, such as 4.5 ml, which is smaller than the amount L1 of the process solution.

Then, as shown in a step S4 of FIG. 8, the secondary process solution containing the precipitated product dissolved therein is analyzed by an inductively coupled plasma mass analyzer (ICP-MS). For example, measurement is performed in terms of the mass $m1(g)$ of a metal impurity (or each metal if a plurality of metals, such as copper and iron, are contained) and the mass $m2(g)$ of quartz contained in the secondary process solution. Then, the measurement values are used to determine the metal impurity concentration in quartz $c(\%)$ $(=m1/(m1+m2)\times100)$. The mass of each metal impurity contained in the secondary process solution is as small as the order of nano-grams (ng), and thus the metal impurity concentration in quartz is in the order of ppb, for example.

According to the method described above, the mass of quartz etched from the examination objective portion is determined on the basis of quartz dissolved in the secondary process solution. Alternatively, the mass of quartz etched from the examination objective portion may be determined by the following method. Specifically, when the primary process solution used for etching is transferred from the examination assistant device to another container, such as the evaporating pan 61, the process solution is divided into two parts for metal analysis and quartz analysis, which are then transferred into different containers. The primary process solution in one of the containers is evaporated and dried, and is then supplied with the secondary process solution to determine the mass of a metal, as described above. The primary process solution in the other container is evaporated and dried in the same manner, and is then supplied with a process solution having a composition the same as or different from the secondary process solution to determine the mass of quartz.

According to the embodiments described above, the examination assistant device 3 or 4, which can be placed at an arbitrary position, is used to immerse a part of the quartz product in a process solution consisting of an etching solution. Then, a metal dissolved in the process solution is identified. Accordingly, when an examination objective portion of a quartz product, such as the reaction tube 1 or wafer boat 2, is examined, there is no need to crush the quartz product or cut out a part of the quartz product. It is thus possible to analyze a new quartz product or cleaned quartz product by means of nondestructive examination to guarantee that the content of metal impurity is within acceptable values for the product. Using such a guaranteed quartz product, metal contamination of a wafer W is prevented. Further, the metal impurity concentration of an examination objective portion can be measured at a pinpointed location, which simplifies sampling and improves workability.

In the examination, since no metal is dissolved in the process solution from a portion other than an examination objective portion (surface) of a quartz product, the examination objective portion can be analyzed with high accuracy. Particularly, the grooves 22 formed in the supporting struts 21 of the wafer boat 2 are portions that were brought into contact with a metal working tool in machining quartz, while they are configured to come into contact with wafers W. Accordingly, the metal impurity concentration of the surface layer of the grooves 22 in particular have to be measured with high accuracy. In light of this fact, the examination assistant device 3 can prove to be very effective.

According to the embodiments described above, the primary process solution is evaporated and dried to precipitate metal, and the precipitated product is dissolved into the secondary process solution in an amount smaller than that of the primary process solution. In this case, the analysis performed by an ICP-MS has to handle only a small amount of solvent for dissolving metal, which can reduce the analysis error. Specifically, the amount of metal dissolved in the primary process solution is very small, and the metal concentration may be lower than the lower detection limit of an analyzer. In this respect, where the amount of solvent is set to be small, as in the secondary process solution, the apparent value of the metal impurity concentration can be higher. Consequently, for example, even where the concentration of metal dissolved in the primary process solution is close to the lower detection limit of an analyzer, the concentration can be increased to a level to obtain a reliable analysis result. In other words, where the amount of solvent is set to be small, as in the secondary process solution, it is possible to use an inexpensive apparatus with a high value of the lower detection limit.

According to the embodiments described above, hydrogen fluoride contained at a high concentration in the primary process solution is evaporated, and the solvent is switched to the secondary process solution containing, e.g., 0.1 wt % or less of diluted hydrofluoric acid. In this case, during analysis, a smaller amount of hydrogen fluoride matches with the vapor pressure of evaporation from the solvent, and thus the mass spectrum interference caused by hydrogen fluoride is suppressed. Consequently, the analysis can be performed with higher accuracy while reducing the analysis error.

According to the embodiments described above, the etching is performed to obtain an etching depth of 1 μm with reference to the relationship between the composition of the process solution (etching solution) and the process time. In this case, since analysis can be performed for every 1 μm-depth, it is possible to analyze with high accuracy a metal impurity contained in a very thin layer near the surface, where the metal impurity is easily deposited. Further, there is no need to use a film thickness measuring tool or the like to measure the actual etching depth for every analysis, which can shorten the analysis time. Furthermore, the relationship between the etching time and etching depth is in linear correlation at various values of hydrofluoric acid concentration. Accordingly, the etching depth can be selected or controlled within a range of, e.g., 1 to 10 μm by adjusting the process time.

Figure 9A:
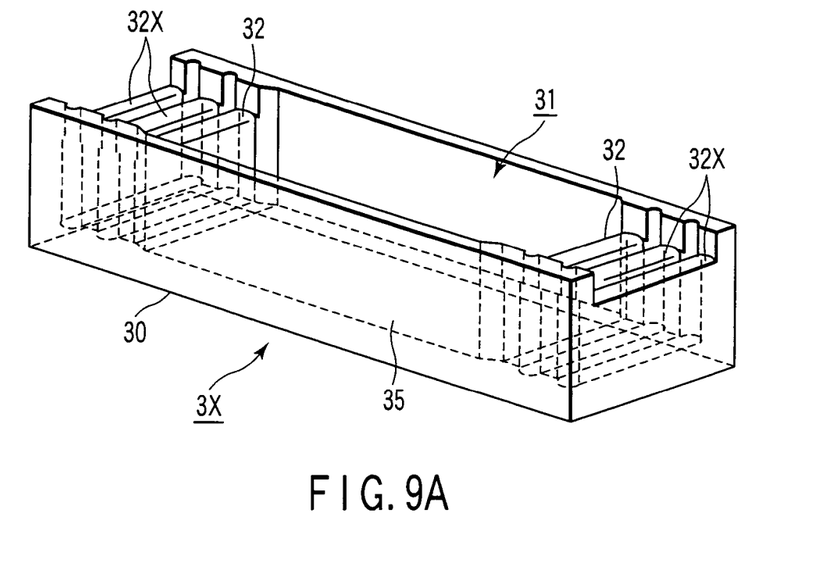
FIG. 9A is a perspective view showing another examination assistant device used for examination to identify a metal impurity contained in the surface layer of a supporting strut of the wafer boat.
Figure 9B:
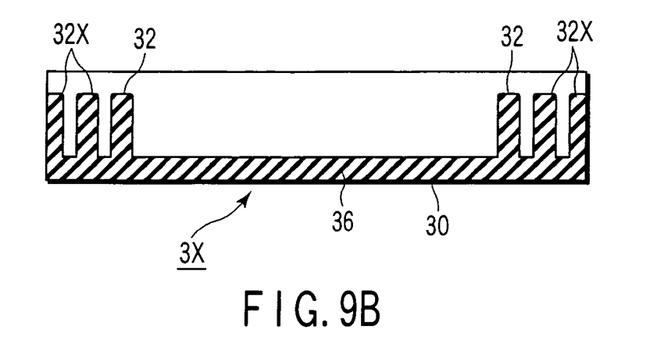
FIG. 9B is a sectional side view of the examination assistant device shown in FIG. 9A.
Figure 9C:
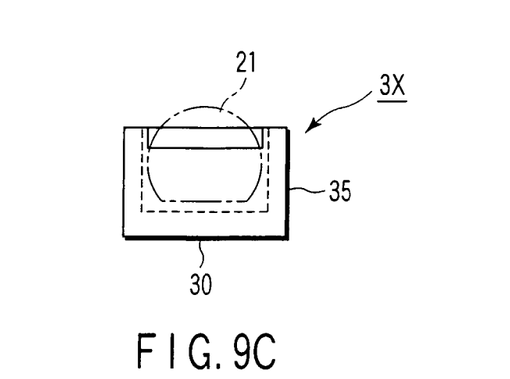
FIG. 9C is an end side view of the examination assistant device shown in FIG. 9A.

FIGS. 9A to 9C are a perspective view, a sectional side view, and an end side view, respectively, showing another examination assistant device 3X used for examination to identify a metal impurity contained in the surface layer of a supporting strut 21 of the wafer boat 2. As shown in FIGS. 9A to 9C, the examination assistant device 3X does no include the latches 32 of the examination assistant device 3 shown in FIGS. 3A to 3C. Alternatively, the examination assistant device 3X includes a plurality of engaging plates 32X disposed outside a pair of end plates 32. The pair of end plates 32 and engaging plates 32X are arranged to be inserted into grooves 22 of the supporting strut 21 so that they come into close contact and engage with the grooves 22. The examination assistant device 3X is attached to the supporting strut 21 by this close-contact engagement (the surface frictional force) of the end plates 32 and engaging plates 32X with the grooves 22. If the examination assistant device can be attached to the supporting strut 21 solely by used of the close-contact engagement of the end plates 32 with the grooves 22, the engaging plates 32X may be omitted.

When the examination assistant device 3X is used for examination, at first, the examination assistant device 3X is attached to the supporting strut 21 in a horizontal state, as described above with reference to FIGS. 5A to 5C. Then, the process solution consisting of an etching solution is supplied into the solution receiver 31 of the examination assistant device 3X, so that an examination objective portion (a portion of the supporting strut 21 including grooves 22) is immersed in the process solution. The solution receiver 31 may be supplied with a predetermined amount of the process solution before the examination assistant device 3X is attached to the supporting strut 21a. After the etching by the process solution is performed for a predetermined time, the process solution used for the etching is analyzed in accordance with the sequence shown in FIGS. 8A to 8D.

Figure 10A:
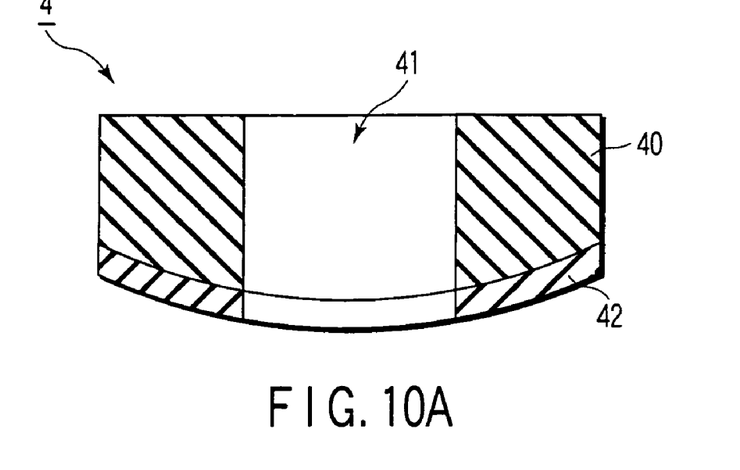
FIG. 10A is a perspective view showing another examination assistant device used for examination to identify a metal impurity contained in the surface layer of an curved inner surface of the reaction tube.
Figure 10B:
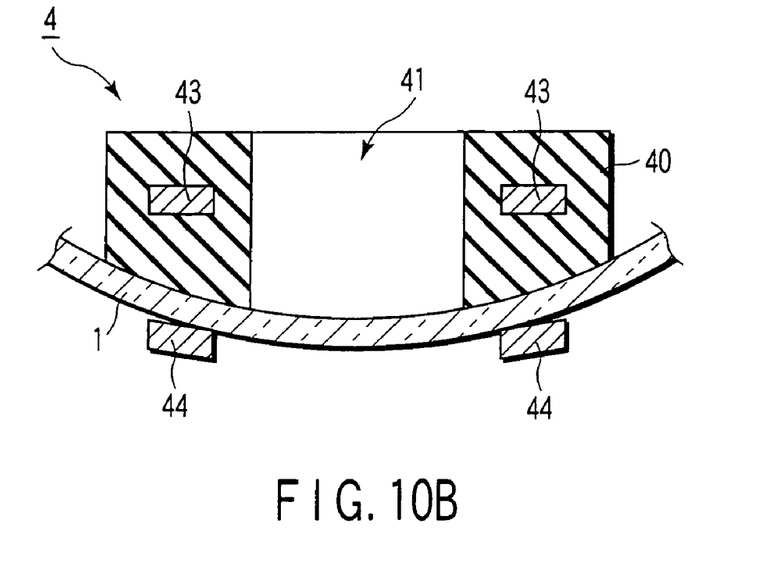
FIG. 10B is a perspective view showing a further examination assistant device used for examination to identify a metal impurity contained in the surface layer of an curved inner surface of the reaction tube.

FIGS. 10A and 10B are perspective views showing other examination assistant devices 4X and 4Y used for examination to identify a metal impurity contained in the surface layer of a curved inner surface of the reaction tube 1. In the case of the examination assistant device 4X shown in FIG. 10A, for example, an annular member 40 is provided with an elastic seal member 42 disposed on the bottom. When the annular member 40 is pressed from above to bring the seal member 42 into close contact with the reaction tube 1, a solution receiver 41 can be formed with higher liquid-tightness.

In the case of the examination assistant device 4Y shown in FIG. 10B, an annular member 40 is provided with a magnet 43 embedded therein. In this case, another magnet 44 is used to fix the annular member 40 by magnetic force wherein the magnet 44 is disposed to face the annular member 40 with the reaction tube 1 interposed therebetween. Another fixing means may be used to fix the annular member 40 to the reaction tube 1. Where the annular member 40 is fixed, the annular member 40 does not cause positional shift during a period from supply of the process solution to elapse of a predetermined process time. In this case, quartz of a portion other than the examination objective portion is prevented from being dissolved into the solution. Further, the labor involved in an operator having to hold the annular member 40 by hand is avoided.

The shape of annular member 40 is not limited to a ring, and it may be rectangular in plan form. The annular member may be modified to examine the outer surface of the reaction tube 1. In this case, the bottom of the annular member 40 is formed as a concave curved surface, which is a complementary shape to the curved outer surface of the reaction tube 1.

The mass of quartz etched by the primary process solution may be obtained without relying on data obtained by an analyzer. For example, the area of a portion immersed in the process solution and the etching depth (1 μm in the embodiments described above) are used to mathematically calculate an etched volume. Then, the etched volume is multiplied by the density of quartz to produce a value, which is then presumed as the mass of quartz.

The primary process solution may be not completely evaporated to precipitate quartz and metal impurity. For example, a certain amount of the solution may be evaporated to reduce the amount to form a condensed solution, which is then analyzed. Also with this arrangement, since the amount of the process solution is small, the effects of the same kind described above can be obtained. Further, in order to reduce the analysis error of an ICP-MS due to the influence of hydrogen fluoride, as described above, the collected process solution may be supplied with, e.g., an alkaline component to decompose hydrogen fluoride.

EXPERIMENT

Experiments are conducted to confirm the effects of the embodiments described above.

Experiment 1

In the experiment 1, lower detection limits of an ICP-MS for various metals were measured. At first, sample solutions (corresponding to the process solution) were prepared, such that they contained a predetermined amount of quartz and predetermined amounts of reagent copper to set the copper concentration at different values. Then, each sample solution was evaporated and dried to precipitate copper, which was then dissolved in a solvent to form a diluted sample solution. The sample solution was then analyzed by the ICP-MS to determine the mass of copper and the mass of quartz. Based on this analysis result, the lower detection limit was defined to be at the minimum concentration value among values that were converted into the copper concentration in quartz and agreed with the known concentration value. The same operation was also performed for each of sodium (Na), aluminum (Al), chromium (Cr), iron (Fe), nickel (Ni), and zinc (Zn).

Experiment 2

In the experiment 2, the same operation as in the experiment 1 was performed except that each sample solution was directly analyzed by an AAS.

Result and Review of Experiments 1 and 2

Figure 11:
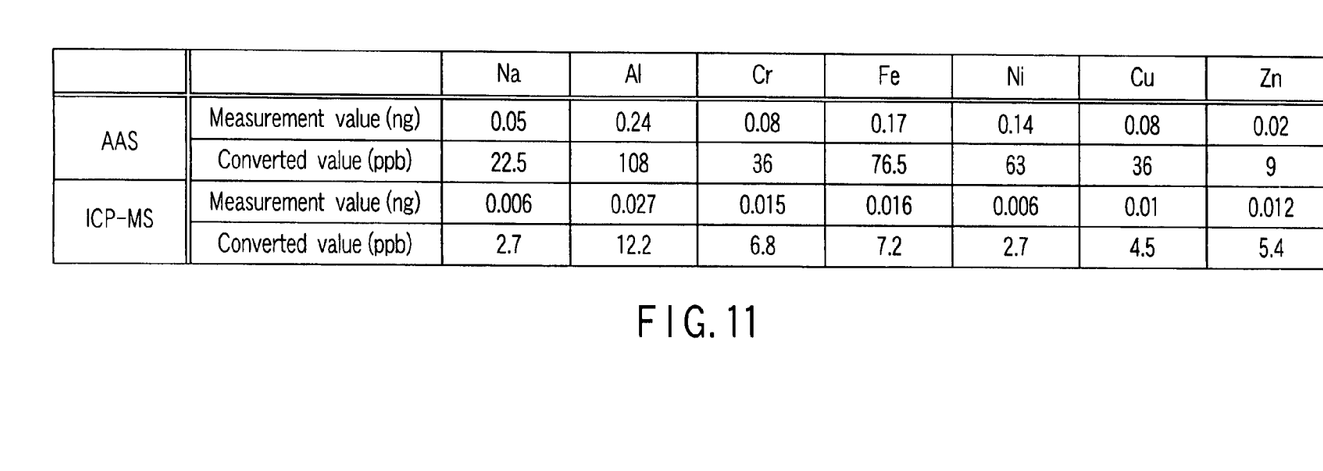
FIG. 11 is a characteristic view showing lower detection limits of an ICP-MS and an AAS obtained by experiments 1 and 2.

FIG. 11 is a characteristic view showing lower detection limits of the ICP-MS and AAS obtained by the experiments 1 and 2. As shown in the result, looking at copper for example, the AAS lower detection limit was 36 ppb, while the ICP-MS lower detection limit was 4.5 ppb, which was far lower than the former one. As regards the other metals, the ICP-MS lower detection limits were far lower than those of the AAS. Specifically, it has been confirmed that analysis using the ICP-MS can be performed with very high accuracy.

However, if high concentration hydrofluoric acid without being evaporated or dried is directly analyzed by the ICP-MS, analysis errors may occur, as described above. The experiments 1 and 2 did not include such analysis results for comparison, because they were not reliable. Specifically, it is possible to improve the reliability of an ICP-MS analysis technique by performing the step of evaporating and drying the solution.

INDUSTRIAL APPLICABILITY

With an examination method and examination assistant device according to the present invention, it is possible to identify, by means of nondestructive examination, a metal impurity contained in an examination objective portion of a quartz product used in a semiconductor processing apparatus.

The invention claimed is:

1. In combination an examination assistant device and a part of a quartz product of a semiconductor processing apparatus, said device holding a process solution including an etching solution in contact with the part, the quartz product being a pole member having a plurality of grooves for supporting target substrates to be processed in the semiconductor processing apparatus,
   the device being configured to treat, as an examination objective portion, a portion of the pole member present between a pair of concave portions, which are two of the grooves, the device comprising:
   a pair of end plates configured to engage with the pair of concave portions;
   a frame connecting the pair of end plates; and
   a solution receiver disposed between the pair of end plates, the solution receiver having dimensions for storing the process solution in a predetermined amount to hold the process solution in contact with the examination objective portion to etch the examination objective portion.

2. The device according to claim 1, further comprising a pair of latches to attach the device to the pole member, such that the pole member is pinched between the pair of latches and the pair of end plates.

3. The device according to claim 2, wherein each of the latches is pivotally supported on the frame and rotatable between a position to attach the device to the pole member and a position to detach the device from the pole member.

4. The device according to claim 1, wherein the device is attached to the pole member by close-contact engagement of the pair of end plates with the pair of concave portions.

5. The device according to claim 1, further comprising, in addition to the pair of end plates, a plurality of engaging plates to be inserted into the grooves, wherein the device is attached to the pole member by close-contact engagement of the pair of end plates and the engaging plates with the grooves.

6. The device according to claim 1, wherein the solution receiver is defined by a space in a container formed by the pair of end plates and the frame.

7. The device according to claim 6, wherein the pair of end plates and the frame consist essentially of fluoroplastic.

8. An examination method for examining part of a quartz product of a semiconductor processing apparatus by use of a process solution including an etching solution, the quartz product being a pole member having a plurality of grooves for supporting target substrates to be processed in the semiconductor processing apparatus, the method comprising:
   preparing an examination assistant device configured to treat, as an examination objective portion, a portion of the pole member present between a pair of concave portions, which are two of the grooves, the device comprising a pair of end plates configured to engage with the pair of concave portions, a frame connecting the pair of end plates, and a solution receiver disposed between the pair of end plates, such that the solution receiver has dimensions for storing the process solution in a certain amount to hold the process solution in contact with the examination objective portion and to etch the examination objective portion,
   placing the examination assistant device on the pole member such that the pair of end plates engages with the pair of concave portions and the examination objective portion is positioned within the solution receiver;

causing the process solution within the solution receiver to be in contact with the examination objective portion for a predetermined time, thereby performing etching on the examination objective portion; and operating an analyzer to analyze the process solution used for the etching to identify a metal impurity contained in the examination objective portion.

9. The method according to claim 8, wherein said identifying the metal impurity contained in the examination objective portion comprises:

evaporating and drying the process solution used for the etching to precipitate quartz and the metal impurity to form a precipitated product;

dissolving the precipitated product into a secondary process solution comprising an etching solution and set to be in an amount smaller than that of the process solution; and operating the analyzer to analyze the secondary process solution containing the precipitated product dissolved therein.

10. The method according to claim 8, wherein said identifying the metal impurity contained in the examination objective portion comprises:

condensing the process solution used for the etching to form a condensed solution; and operating the analyzer to analyze the condensed solution.

11. The method according to claim 8, wherein said identifying the metal impurity contained in the examination objective portion is performed by an inductively coupled plasma mass analyzer.

12. The method according to claim 8, wherein the predetermined time for performing the etching on the examination objective portion is determined to correspond to a target etching depth, with reference to a relationship prepared in advance between process time and quartz etching amount in etching quartz by the etching solution.

13. The method according to claim 8, wherein said identifying the metal impurity contained in the examination objective portion comprises:

analyzing the process solution used for the etching to detect an amount of quartz and an amount of the metal impurity; and using the amount of quartz and the amount of the metal impurity to estimate a concentration of the metal impurity in the examination objective portion.

14. An examination method for examining part of a quartz product of a semiconductor processing apparatus by use of a process solution including an etching solution, the quartz product being a reaction tube of the semiconductor processing apparatus, the method comprising:

preparing an examination assistant device configured to treat, as an examination objective portion, a portion of a curved surface of the reaction tube, the device comprising an annular member having a bottom surface to come into close contact with the curved surface, and configured to cooperate with the curved surface to form a solution receiver that surrounds the examination objective portion, and an elastic seal member disposed on the bottom surface, such that the annular member has dimensions for forming the solution receiver to store the process solution in a certain amount to hold the process solution in contact with the examination objective portion and to etch the examination objective portion;

placing the examination assistant device on the curved surface of the quartz reaction tube and forming the solution receiver such that the examination objective portion is positioned within the solution receiver;

causing the process solution within the solution receiver to be in contact with the examination objective portion for a predetermined time to perform etching on the examination objective portion; and operating an analyzer to analyze the process solution used for the etching, to identify a metal impurity contained in the examination objective portion.

15. The method according to claim 14, wherein the annular member consists essentially of fluoroplastic.

16. The method according to claim 14, wherein the annular member further comprising a magnet embedded therein.

17. The method according to claim 14, wherein said identifying the metal impurity contained in the examination objective portion comprises:

evaporating and drying the process solution used for the etching to precipitate quartz and the metal impurity to form a precipitated product;

dissolving the precipitated product into a secondary process solution comprising an etching solution and set to be in an amount smaller than that of the process solution; and operating the analyzer to analyze the secondary process solution containing the precipitated product dissolved therein.

18. The method according to claim 14, wherein said identifying the metal impurity contained in the examination objective portion comprises:

condensing the process solution used for the etching to form a condensed solution; and operating the analyzer to analyze the condensed solution.

* * * * *